United States Patent
Kaethner et al.

(10) Patent No.: US 12,142,365 B2
(45) Date of Patent: Nov. 12, 2024

(54) METHOD FOR REGISTRATION OF IMAGE DATA AND FOR PROVISION OF CORRESPONDING TRAINED FACILITIES, APPARATUS FOR DOING SO AND CORRESPONDING COMPUTER PROGRAM PRODUCT

(71) Applicant: Siemens Healthcare GmbH, Erlangen (DE)

(72) Inventors: Christian Kaethner, Forchheim (DE); Alois Regensburger, Poxdorf (DE)

(73) Assignee: Siemens Healthineers AG, Forchheim (DE)

( * ) Notice: Subject to any disclaimer, the term of this patent is extended or adjusted under 35 U.S.C. 154(b) by 327 days.

(21) Appl. No.: 17/116,190

(22) Filed: Dec. 9, 2020

(65) Prior Publication Data
US 2021/0174523 A1 Jun. 10, 2021

(30) Foreign Application Priority Data
Dec. 10, 2019 (DE) ...................... 10 2019 219 246.7

(51) Int. Cl.
*G16H 30/40* (2018.01)
*G06F 18/214* (2023.01)
(Continued)

(52) U.S. Cl.
CPC ........... *G16H 30/40* (2018.01); *G06F 18/214* (2023.01); *G06F 18/22* (2023.01); *G06T 7/0012* (2013.01);
(Continued)

(58) Field of Classification Search
CPC ......... G06T 7/337; G06T 7/0012; G06T 7/11; G06T 2207/10081; G06T 2207/10088;
(Continued)

(56) References Cited

U.S. PATENT DOCUMENTS

| | | | |
|---|---|---|---|
| 7,916,919 B2* | 3/2011 | Zheng | G06V 10/7715 |
| | | | 382/128 |
| 8,126,239 B2* | 2/2012 | Sun | A61B 6/12 |
| | | | 600/407 |

(Continued)

FOREIGN PATENT DOCUMENTS

| WO | 2018015414 A1 | 1/2018 |
| WO | 2019219387 A1 | 11/2019 |

OTHER PUBLICATIONS

German Office Action for German Application No. 10 2019 219 246.7 dated Aug. 31, 2020.

*Primary Examiner* — Qun Shen
(74) *Attorney, Agent, or Firm* — Lempia Summerfield Katz LLC (57) ABSTRACT

A system and method for registration of preoperative image data of a patient with less high-quality intra-operative image data relative to the data. Predetermined anatomical landmarks and/or an anatomical variant are identified in the image data by machine-learning facilities. At least one of the machine-learning facilities is trained patient-specifically and/or specifically for an anatomical variant of the patient to be examined. The registration is then carried out with the aid of the landmarks identified.

22 Claims, 3 Drawing Sheets

(51) Int. Cl.
| | |
|---|---|
| *G06F 18/22* | (2023.01) |
| *G06T 7/00* | (2017.01) |
| *G06T 7/11* | (2017.01) |
| *G06T 7/33* | (2017.01) |
| *G06V 10/26* | (2022.01) |
| *G06V 10/44* | (2022.01) |
| *G06V 10/764* | (2022.01) |
| *G06V 10/774* | (2022.01) |
| *G06V 10/776* | (2022.01) |
| *G06V 10/80* | (2022.01) |
| *G06V 10/82* | (2022.01) |
| *G16H 50/20* | (2018.01) |

(52) U.S. Cl.
CPC ............... *G06T 7/11* (2017.01); *G06T 7/337* (2017.01); *G06V 10/26* (2022.01); *G06V 10/44* (2022.01); *G06V 10/764* (2022.01); *G06V 10/774* (2022.01); *G06V 10/776* (2022.01); *G06V 10/803* (2022.01); *G06V 10/82* (2022.01); *G16H 50/20* (2018.01); *G06T 2207/10081* (2013.01); *G06T 2207/10088* (2013.01); *G06T 2207/20081* (2013.01); *G06T 2207/30101* (2013.01); *G06V 2201/03* (2022.01)

(58) Field of Classification Search
CPC ........... G06T 2207/20081; G06T 2207/30101; G16H 50/20; G16H 30/40; G06K 9/6215; G06K 9/6256; G06V 2201/03
See application file for complete search history.

(56) References Cited

U.S. PATENT DOCUMENTS

| | | | |
|---|---|---|---|
| 2013/0129174 A1* | 5/2013 | Grbic | G06T 7/344 382/131 |
| 2013/0294667 A1* | 11/2013 | Zheng | G06T 7/30 382/131 |
| 2014/0003700 A1* | 1/2014 | Hermosillo Valadez | G06T 7/0014 382/131 |
| 2016/0100909 A1* | 4/2016 | Wollowick | G16H 40/63 600/424 |
| 2017/0213339 A1* | 7/2017 | Hibbard | G06T 7/11 |
| 2017/0277981 A1* | 9/2017 | Zhou | G06T 7/143 |
| 2018/0150929 A1* | 5/2018 | Pheiffer | A61B 34/10 |
| 2018/0240219 A1* | 8/2018 | Mentl | G06T 11/008 |
| 2019/0130587 A1* | 5/2019 | Kurzendorfer | G06T 3/14 |
| 2019/0205606 A1* | 7/2019 | Zhou | G06N 3/0445 |
| 2019/0336109 A1* | 11/2019 | Pheiffer | G06T 7/344 |
| 2020/0380687 A1* | 12/2020 | Avital | A61B 8/5207 |
| 2021/0110605 A1* | 4/2021 | Haslam | B33Y 50/00 |

* cited by examiner

METHOD FOR REGISTRATION OF IMAGE DATA AND FOR PROVISION OF CORRESPONDING TRAINED FACILITIES, APPARATUS FOR DOING SO AND CORRESPONDING COMPUTER PROGRAM PRODUCT

CROSS REFERENCE TO RELATED APPLICATIONS

This application claims the benefit of DE 102019219246.7 filed on Dec. 10, 2019, which is hereby incorporated by reference in its entirety.

FIELD

Embodiments relate to a method for registration of image data and to a method for provision of corresponding trained machine-learning facilities.

BACKGROUND

There are many ways in which imaging is employed in current medical practice. It is thus known for example that image data of a patient may be recorded for diagnostic purposes or also for treatment or intervention planning before an actual intervention. Such image data, for example a preoperative CT or MR dataset (CT: Computed Tomography, MR: Magnetic Resonance), may be of high quality, for example, may include a good image quality, resolution, accuracy, signal-to-noise ratio, contrast and/or more besides. Recording this kind of high-quality data may be associated with a considerable effort however, for example a relatively long recording time, a relatively high dose of contrast medium and/or a relatively high dose of radiation and/or require a relatively cramped and hard to access diagnostic imaging system.

Because of the relatively great effort or the relatively high stress for the patient, high-quality imaging is typically not used intra-interventionally or intra-operatively, for example, during an intervention, but rather an intra-operative imaging with relatively lower or inferior quality or image quality is then used.

In order to be able to use as much information and the most accurate information or image data possible during the respective intervention, relatively high-quality preoperative image data and less high-quality intra-operative image data relative thereto may be registered with one another and then combined with one another, for example overlaid on one another. However, this is often difficult in practice, for example as a result of the inferior image quality of the intra-operative image data, because of deformations or changes of the patient body by comparison with a point at which the preoperative image data was recorded and more besides. Previous solutions are therefore disadvantageously less robust and/or associated with great effort as a result of the anatomical variability to be observed from patient to patient.

For a selective contrast a catheter, for example, may be guided to an organ to be examined, for example the liver, and an intra-operative dataset recorded with highly concentrated selectively injected contrast medium. Corresponding vessels may then be segmented by threshold values or may be visualized by windowing. The method typically requires an interventional radiologist in addition to a surgeon undertaking the treatment in each case and may be relatively time-consuming and possibly lead to complications. As an alternative for example a systemic contrast could be used as part of a 3D DSA technique (DSA: Digital Subtraction Angiography). In this case a contrast medium may be injected via a vein, in the arm for example, and after a defined time an intra-operative x-ray image may be recorded. The disadvantage however is that typically a relatively high dose of contrast medium would be necessary, in order still to be able to visualize liver vessels by windowing. With a dose of contrast medium more able to be borne by the patient on the other hand the HU or contrast differences of the corresponding vessels are often too small for a reliable, accurate or robust segmentation or registration. Moreover, because of an additional mask pass, a doubling of the x-ray dose is necessary and, even with occasional holding of the breath—possibly lasting twice as long as usual—movement artifacts may occur, that may likewise render the segmentation and registration much more difficult. A direct segmentation of a vascular tree for example, because of the low differences in contrast between a respective vessel structure and surrounding tissue in conventional intra-interventional x-ray imaging, is on the other hand not possible or only possible for relatively large vessels.

BRIEF SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide support during intra-operative imaging that is able to be used easily by medical personnel and at the same time is robust.

A method relates to a registration of preoperative image data provided of a patient to be examined with intra-operative image data provided of the patient of less high quality compared thereto. The intra-operative image data of the patient thus has a lower or inferior image quality than the preoperative image data. This may mean a lower resolution, an inferior contrast ratio and/or more besides for example.

The method may be entirely or partly a computer-implemented method.

A first machine-learning facility is provided in the method or for the method, that is trained, in correspondingly relatively higher-quality preoperative image data, to identify or to determine predetermined anatomical landmarks, for example, characteristics or features, and/or to identify or to determine a respective anatomical variant present and/or to create and/or to carry out a segmentation of such preoperative image data. This may for example mean that the preoperative image data is classified and/or annotated with the anatomical variant present, for example, imaged, therein or with the anatomical landmarks and/or the segmentation present or imaged therein. Likewise, the identified anatomical landmarks and/or the segmentation or possibly segmentation or region boundaries that have been determined or identified during the segmentation, are marked by the first facility for example and/or corresponding coordinates or positions of the identified landmarks and/or of details of the segmentation may be determined, for example in the coordinate system of the image data or in another predetermined coordinate system. Details of the segmentation may be or include region or tissue boundaries or courses, contiguous regions, region shapes and/or more besides.

In the method or for the method a second machine-learning facility is further provided for the respective patient to be examined, that is trained patient-specifically and/or specifically for the anatomical variant of the respective patient to be examined, to identify or to determine anatomical landmarks, for example the same anatomical landmarks already mentioned, in correspondingly less high-quality intra-operative image data and/or to create or carry out a segmentation of such intra-operative image data. The second facility may be configured to determine and specify coordinates or positions of the identified landmarks and/or for example segmentation boundaries or details or to mark them in the image data.

Because the second facility is trained specifically for the anatomical variant or patient-specifically for the respective patient to be examined may mean for example that the second facility is adapted for identifying the landmarks and/or for segmentation of image data of precisely the specific anatomical variant or to individual characteristics of the respective patient to be examined, for example, has correspondingly adapted part algorithms, structures, weights, filters and/or more besides. To this end the second facility may be trained for example with corresponding patient-specific training data or with training data containing or imaging the specific anatomical variant. By contrast the first facility may be trained less specifically or non-specifically, for example not specifically for a patient or a variant, for example, not be trained or adapted to an individual patient or a specific anatomical variant.

If the first machine-learning facility is trained to identify the anatomical landmarks, in a method step of the method in the preoperative image data provided of the respective patient to be examined, anatomical landmarks present or predetermined are identified, for example, determined, or detected by it. If the first machine-learning facility is trained for segmentation, in a method step of the method, the preoperative image data provided of the respective patient to be examined is segmented, for example, a segmentation is created or determined for them by it. This may, for example, mean or include a recognition of contiguous areas of tissue, tissue or region boundaries, courses of anatomical features and/or more besides.

If the first machine-learning facility is trained to identify the anatomical variant, in a method step of the method, at least on the basis of the preoperative image data of the respective patient to be examined, its anatomical variant is identified, for example, determined, or detected by it. In this case the preoperative image data of the patient to be examined may for example be annotated and/or classified in accordance with the identified anatomical variant. Likewise, disease pathologies, such as fatty liver or cirrhosis of the liver, past therapies, such as for example chemotherapy or embolization, and/or other data, for example size, weight, body composition, or the like, of the patient may be provided or captured as features or data and taken into account in the determination or classification of the anatomical variant, for example, used. This may lead or contribute to a more precise and/or more reliable determination or classification of the anatomical variant.

Where necessary the predetermined anatomical landmarks—where present—are then identified in the preoperative image data of the respective patient to be examined, for example, determined, or detected. In addition, or as an alternative a segmentation of the preoperative image data of the respective patient to be examined is created or carried out. A third machine-learning facility provided is used for this recognition of the landmarks or for this segmentation. The third machine-learning facility is trained to identify the predetermined landmarks and/or for segmentation specifically for preoperative image data of this anatomical variant. In a similar way to that described in conjunction with the second facility, the third facility may thus be configured specifically to the respective anatomical variant, for example trained or retrained for this anatomical variant, for example with the aid of preoperative image data.

In a further method step of the method the predetermined anatomical landmarks—where present—are identified in the intra-operative image data of the respective patient to be examined by the second machine-learning facility, for example, determined or detected and/or the segmentation for the intra-operative image data of the respective patient to be examined is created or carried out by the second machine-learning facility.

In a further method step of the method the registration of the preoperative image data of the patient to be examined with the intra-operative image data of the patient to be examined may be carried out where necessary with the aid of the anatomical landmarks identified in this way by the first facility or by the third facility in the preoperative image data of the respective patient to be examined and by the second facility in the intra-operative image data of the respective patient to be examined. In addition, or as an alternative the registration may be carried out with the aid of the segmentations of the preoperative and intra-operative image data. The landmarks or segmentations or corresponding coordinates or positions or details may be used as a reference. For the registration the identified landmarks or region boundaries or courses of the intra-operative image data or of their coordinates or positions may thus be aligned to the corresponding landmarks or region boundaries or courses or to corresponding coordinates or positions of the preoperative image data. In such cases registration methods known from medical imaging or image processing technology may be used. In this way the registration may be done strictly or elastically for example, thus in the latter case for example may include a deformation or distortion of the image data, to achieve a precise and spatially consistent registration.

A corresponding result of the registration or of the method may then be output or provided via a corresponding output interface and/or stored in a data memory. Such a result, for example, corresponding result data, may be or may include a specification or set of rules for the relative alignment, displacement and/or transformation of the image data, an overlay image from the preoperative and the intra-preoperative image data registered thereto (overlay) and/or more besides.

Where segmentations of the respective image data are carried out in the method, these may be provided independently of the registration or without carrying out the registration as a self-contained result. Segmentations or corresponding segmentation data may be used, reused, or reprocessed in a wide variety of ways.

Then for example, on the basis of the respective result, further processing of the preoperative and/or the intra-operative image data, path planning, instrument or therapy guidance or navigation and/or more besides may be carried out or supported.

In an embodiment, with the second facility and possibly with the third facility, an overfitting to the specific patient to be examined in each case or to the specific anatomical variant is brought about. An overfitting is always avoided with conventional machine-learning methods and facilities, since the corresponding methods and facilities conventionally function for all patients, for example, ought to be able to be universally applicable. However, one finding is that, with the advance of technology, for example of the hardware for machine-learning facilities as well as the understanding thereof, options become practicable, such as for example the creation and use of patient- or variant-specific facilities, for example corresponding neural networks. A further finding is that, by contrast with previous methods or approaches, a marked improvement may be achieved if the universality of all details or stages, for example, the universal applicability not of the method per se, but at least of a trained machine-learning facility used therein is dispensed with. Ultimately this provides a far more robust registration for the intra-operative imaging despite its relatively inferior image quality and the wide variety of anatomical variants or patient-specific versions or characteristics that occur in practice to be achieved.

This robustness, that may be achieved is not able to be achieved in practice with a single universal, for example, non-specific, machine-learning facility, not least because of the limited amount of available training data in practice and the effort associated therewith.

Embodiments make it possible for example to use relatively fast and low-stress intra-operative imaging, for example intra-operative x-ray imaging, that is also referred to by the name DynaCT, with systemic contrast for vascular issues during image-guided interventions. In such cases for example a catheter does not have to be navigated, so that the corresponding method may be carried out easily and with little effort themselves for example by the respective surgeon conducting the treatment. In such cases an easy-to-handle C-arm x-ray device able to be integrated into medical or interventional workflows may be used intra-operatively for example, for example, no imaging of the respective patient by a more complex fully functional tube or spiral CT scanner and accordingly no significant interruption of the intervention is necessary. Moreover, a reliable registration with a medium contrast dose for the systemic contrast reduced by comparison with conventional approaches may be achieved and thus stress on the respective patient may be reduced.

Embodiments may be employed for liver examinations or liver interventions, but are not restricted to this however but may likewise be used for other regions or organs, for example the brain or the like.

Any surgical steps or measures mentioned or indicated for explanation may not be part of the method. Embodiments, for example including the method, are thus only claimed in as far as the method does not include any surgical step. This does not run counter to an ability to be carried out or applied however, since the method may be employed in parallel to an intervention or a surgical intervention, but in this event, it merely serves for, for example automatic or semi-automatic, support of respective medical personnel and may likewise be carried out or applied independently of the actual surgical steps undertaken, for example on the basis of corresponding data provided. Even if the method may be carried out to advantage at least partly during an interventional or surgical procedure, it ultimately merely relates to a corresponding control or a corresponding operation of an apparatus or a data processing facility and not to the surgical steps that might possibly be carried out during the procedure or the intervention.

The machine-learning facilities mentioned herein may each be or include a trainable algorithm, an, for example deep, for example, multilayer, artificial neural network, a Support Vector Machine (SVM), a decision tree and/or the like. The machine-learning facilities may be based on k-means clustering, Temporal Difference (TD) learning, for example Q learning, a genetic algorithm and/or association rules or an association analysis. The machine-learning facilities may for example be or include a (deep) convolutional neural network (CNN), a (deep) adversarial neural network, a (deep) generative adversarial neural network (GAN) and/or more besides.

The machine-learning facilities may be present entirely or in part in the form of a corresponding computer program or program code, but may likewise include hardware, for example, assemblies or components configured or configured for its execution. The latter may be a data memory, on which a corresponding program code or a corresponding computer program is stored, and also possibly a processor associated therewith for executing the computer program or program code.

The machine-learning facilities may include corresponding software and/or hardware interfaces for receiving input data and for output of result or output data that has been created by processing the input data.

The preoperative image data may be a respective CT or MR dataset or include such a set for example. A preoperative CT dataset may be recorded by a tube or spiral CT scanner for example and exhibit an accordingly relatively high image quality.

By contrast the intra-operative image data may include one or more intra-operative or intra-interventional x-ray images for example, that are recorded or have been recorded for example by a relatively less complex or less accurate C-arm x-ray device and therefore may include a relatively inferior image quality.

The intra-operative image data may likewise be or include ultrasound image data for example. Ultrasound image data may be recorded intra-operatively easily and in a gentle way for the respective patient, but likewise typically has an inferior image quality than for example a preoperatively recorded CT or MR dataset.

The preoperative image data may likewise be 3D image data for example, while the intra-operative image data may be 3D image data or 2D image data. In the latter case the inferior image quality of the intra-operative image data may then already be given in the sense by that fact that, as 2D image data, it contains less information than the preoperative 3D image data.

The preoperative image data and the intra-operative image data may thus each be recorded, and also by comparison with one another, with different imaging modalities.

The machine-learning facilities may be trained for image data of a specific kind or a specific type, for example, for image data recorded by a specific imaging modality. The facilities may be supplied during their training with training image data of the corresponding kind or of the corresponding type. Depending on the application case the various machine-learning facilities may thus be trained for the same or for different kinds or types of image data.

When the preoperative image data and the intra-operative image data are of the same kind or of the same type, the second facility and the third facility may be trained accordingly for the same kind or the same type of image data. Therefore, the second facility and the third facility may be identical in this case, thus for example the second facility or a copy or instance thereof may be used as the third facility.

Correspondingly different, for example, differently trained machine-learning facilities may be created or provided for the different variants or application cases from which those appropriate for the respective application case may then be selected for use, for example automatically.

In the method the preoperative image data is provided or supplied as input data to the first facility. Through processing of the input data, the first facility creates output data, that is provided or output via a corresponding output interface or for example may be tapped off at an output layer consisting of artificial neurons. The output data of the first facility may be marked, annotated, or classified preoperative image data or an output dataset for example, that contains a corresponding marking, annotation, or classification and/or corresponding position or coordinate specification for the landmarks identified and/or the segmentation and/or more besides.

As input data, the third facility may be provided or supplied with the output data of the first facility and also where necessary in addition with the original preoperative image data. Through processing of input data provided or supplied to it, the third facility likewise creates output data. This output data of the third facility, as described, may be marked preoperative image data, in which the identified anatomical landmarks are marked, in which the coordinates or positions of the identified anatomical landmarks are specified or identified and/or in which the segmentation is specified or contained, for example, for example segmentation or region boundaries are specified or marked. Likewise, the output data of the third facility may be an output dataset or include such a dataset, in which the coordinates or positions of the identified landmarks and/or the segmentation or corresponding segmentation data are contained or specified.

The second facility is provided with the intra-operative image data of the patient as its input data. Through processing of the input data, the second facility likewise creates output data. This output data of the second facility may be marked intra-operative image data for example, in which the identified anatomical landmarks or their positions or coordinates and/or the segmentation or corresponding segmentation or region boundaries are marked or specified. Likewise, the output data of the second facility may also be a dataset separate from the image data for example, in which the identified landmarks and/or the segmentation or their positions or coordinates are contained, for example, specified.

The predetermined landmarks may be a set of features or identifiers or anatomical details or may include such an element. Anatomical landmarks may, for example, be vessel branches, where necessary for specific vessel diameters or diameter relationships of the vessels branching or branching off, boundaries of organs or tissue types, junctions or coalescing points of specific tissue types or anatomical objects, such as for example ligaments or nerves or the like, scars, injuries, incisions and/or more besides. The fact that the predetermined anatomical landmarks are identified in the image data does not necessarily mean in the sense that all predetermined anatomical landmarks will be identified in the respective image data, but may mean for example that at least one anatomical landmark, that is contained in the volume or in the set of the predetermined anatomical landmarks, is identified in the image data. In this case, for example, a number of landmarks may be predetermined as a threshold value, that must at least be identified in the respective image data for continuing the method. This provides the reliability of the method or of the registration carried out therewith to be safeguarded or improved.

Different anatomical variants may be differentiated from one another for example by the availability or presence of different sets or combinations of anatomical landmarks, by their relative positions or alignment to one another and/or to one or more other anatomical features, by different sizes or shapes of an organ or tissue section considered in each case, by the presence or absence of pathological changes or injuries or traces of treatment and/or more besides. Thus, for example it is known that the liver may be subdivided into segments or supply areas, that according to normal practice are consecutively numbered in a specific way. An anatomical variant of a specific liver in each case may then be determined or given for example as "liver with typical segment 8", as "liver with divided segment 8", as "liver with combined segments 7 and 8a", as "liver with tumor in segment 4", as "liver with previous hemihepatectomy, and so forth, as well as if necessary, combinations thereof. Likewise, different anatomical variants may be differentiated from one another for example by different segmentations. In such cases for example sizes, shapes, courses and/or a number of segmented regions or anatomical details in different segmentations may be different from one another.

The provision of the trained facilities and also the provision of the image data may mean in the context for example that at least one computer-readable data medium is provided or read out, on which the respective facility and the respective image data are stored, that the respective facility or the respective image data is transferred or detected or received via a corresponding data interface or that the respective facilities or image data are retrieved or read out via a corresponding data interface. Likewise, the provision in the context may mean that the corresponding devices or image data for example are stored in a—volatile or non-volatile—data memory of an apparatus used for carrying out the method or that this data memory is activated or that there is access to this data memory.

The method may be carried out for example by an appropriately configured medical imaging device, by a local data processing facility connected thereto, by a local computer center (on-premise), by a computer or computer center linked via a network (cloud) or by an independent data processing facility. In the latter case the image data and also if necessary, the output or result data created by the method may be transmitted or provided via at least one portable data medium.

Embodiments may be described or explained below for the sake of clarity and ease of understanding (only) with regard to the anatomical landmarks. In this case however, in addition or as an alternative, the segmentation may be employed or used likewise or analogously.

In an embodiment a plurality of datasets of a plurality of patients are provided, wherein each of the datasets contains preoperative image data of precisely one of the plurality of patients in each case, that is annotated at least with the anatomical variant present therein in each case, and intra-operative image data assigned to this, in which, if and/or where present in each case, at least the predetermined anatomical landmarks are annotated and/or the segmentation is specified. A specific dataset thus includes preoperative and intra-operative image data of only precisely one single patient, thus in this context patient datasets are involved. The datasets including preoperative and associated intra-operative image data may be provided for example as training image data for the machine-learning facilities.

Based on the plurality of datasets provided, anatomical variants are determined, for example automatically, that occur in the datasets in each case with at least one predetermined, absolute, or relative frequency, for example, are contained therein. Then, for each of these anatomical variants determined, for example, occurring correspondingly frequently, a respective variant-specific instance of the second facility is provided, for example automatically, that is trained or retrained in each case only with the aid of the intra-operative image data of the corresponding datasets, in which the respective anatomical variant occurs.

For each of the anatomical variants determined, for example, occurring correspondingly frequently, a respective instance of the third facility is also provided, that is trained or retrained in each case only with the aid of the preoperative image data of the corresponding datasets in which the respective anatomical variant occurs.

With the aid of the provided preoperative image data of the patient to be examined, the anatomical variant of the patient to be examined is determined by the first facility. For the recognition of the landmarks in the image data provided and/or for the creation or carrying out of their segmentation for the registration the instances of the second facility and the third facility trained or retrained for the specific anatomical variant of the patient to be examined are selected and used, for example automatically.

In other words, a database or collection with differently adapted second and third facilities may thus be created and/or provided. Variants or instances may already be trained or retrained in advance, for example, before application of the method to the specific patient to be examined, for example preoperatively, with the aid of the datasets provided as training data of the plurality of other patients.

These embodiments may be applied quickly and flexibly for different types of patients, since no patient-specific training or retraining of the machine-learning facilities is necessary for the individual patient to be examined, for example not intra-interventionally. At the same time, embodiments also provide improved accuracy and robustness compared to conventional methods.

Embodiments may be employed for organs or applications of a manageable, for example, relatively restricted, number of possible anatomical variants or of those occurring in practice, for example when there are fewer than 20 or fewer than 10 corresponding frequently occurring anatomical variants.

The method may restrict itself with regard to the machine-learning facilities to their application or use, for example, not include or include their training or retraining. Likewise, this training or retraining, for example, the creation of the machine-learning facilities, may be part of the method.

In an embodiment a plurality of datasets of a plurality of patients is provided, wherein each of the datasets contains preoperative image data and intra-operative image data assigned thereto of precisely one of the plurality of patients. In this case contained in this image data in each case— provided and/or where present—at least the predetermined anatomical landmarks and/or the segmentation are annotated, for example, listed and/or marked or specified. Each dataset thus includes preoperative and intra-operative image data of precisely one single patient in each case, in this case patient datasets are involved. The datasets may be provided, for example, as training image data for the machine-learning facilities.

The predetermined anatomical landmarks are identified and/or the segmentation created or carried out by the correspondingly trained first facility in the preoperative image data of the patient to be examined.

Then correspondingly similar datasets are determined and selected automatically from the plurality of the datasets provided, that in accordance with a predetermined similarity criterion or measure of similarity based on the identified landmarks and/or the segmentation, describe an anatomy similar to the patient to be examined, for example, image or contain it. To identify the anatomical landmarks in the preoperative image data of the patient to be examined and/or for creation of its segmentation the third facility is used, wherein this is only trained or retrained with the aid of the preoperative image data from the selected similar datasets. To identify the anatomical landmarks in the intra-operative image data of the patient to be examined and/or for creation of its segmentation the second facility is used, wherein this is only trained or retrained with the aid of the intra-operative image data from the selected similar datasets.

The datasets from the plurality of provided datasets, that are similar in the respective specific patient to be examined in respect of the anatomy and/or other characteristics, are determined and selected. The second facility and the third facility may then, with the aid of these selected similar datasets, be trained from scratch, for example, from the ground up, for example starting from a random initialization of weights or parameters of the facilities. Likewise, for recognition of anatomical landmarks and/or for segmentation of image data with the aid of different anatomical variants and specific datasets, pre-trained machine-learning facilities may be retrained for creating the second and/or third facility by the selected similar datasets, for example, fitted or overfitted.

For selection of the similar datasets a threshold value for the similarity, for example, the measure of similarity or the fulfillment of the similarity criterion may be predetermined for example. A respective dataset is then selected for example as a similar dataset, when the similarity for this dataset at least reaches the predetermined threshold value. Likewise, for example an absolute or relative number may be predetermined. The datasets corresponding to this number of most similar datasets are selected. Thus, if for example a number N or N % is predetermined, then the N or N % of the datasets with the greatest similarity or the greatest measure of similarity or the greatest fulfillment of the similarity criterion are selected. By analogy the selection may also be inverted, so that the similarity criterion or measure or the predetermined threshold value may likewise be used as an exclusion criterion and not as an inclusion criterion.

The embodiment may then be applied effectively when there is a variance for the organ considered in each case or for the region considered in each case, for example, there are many different anatomical variants occurring, since it may then be difficult or not practicable to provide a sufficiently large basis of training data for each of the variants. The similarity criterion and the corresponding selection of similar datasets, by comparison with conventional methods, then still provides an improved accuracy and robustness to be achieved in the registration of the image data of the respective individual patient to be examined.

A combination of the two embodiments described is possible for example in such a way that the trained or retrained second and third facilities based on the anatomical variant determined may be used as pre-trained starting points, that are then retrained with the aid of the similar datasets determined or vice versa.

The similarity criterion used or evaluated is whether in the datasets the landmarks identified in the preoperative image data of the patient to be examined and/or predetermined regions or details of the segmentation or at least a respective predetermined portion identified or determined therein are contained in the respective dataset. The predetermined portion may relate in this case to certain specific landmarks, certain types of landmarks or a certain number or quantity of landmarks. For example, only those datasets may thus be selected as similar datasets, in which at least certain specific landmarks, at least a certain type of landmark and/or certain number of the predetermined landmarks and/or certain segmentation details or features were identified. this is able to be checked or evaluated easily and quickly, whereby the method may be applied intra-operatively quickly and therefore with little stress for the respective patient to be examined. Moreover, it may be insured that the registration, at least with high probability, may be carried out successfully and accurately and reliably. The robustness of the method may thus be improved or insured.

Embodiments further include where a geometrical or spatial location relationship of a number of anatomical landmarks and/or segmentation details to one another and/or to at least one predetermined anatomy feature or reference point is used or evaluated as a similarity criterion. The similarity is defined or determined not or not just by the presence of the landmarks but by their spatial or local arrangement or distribution. Where necessary this provides a finer distinction between different variants or versions and thus an improved choice or determination of the similar datasets to be obtained. This in its turn may improve the robustness of the method and ultimately the accuracy or reliability of the registration.

In an embodiment those of the predetermined landmarks present in the preoperative image data of the patient to be examined are identified by the first facility and/or the segmentation is carried out or created. On the basis thereof annotated preoperative image data is created with the identified landmarks and/or the segmentation. This may be done by the first facility for example, that may then provide or output as output data the preoperative image data annotated in this way. Likewise, the correspondingly annotated preoperative image data may be created by an annotation facility provided. This may for example process the original preoperative image data and also the output data in the first facility as input data, in order to create the annotated preoperative image data from the data. The annotation facility may be a conventional image or data processing facility or a further machine-learning facility trained accordingly. The identified landmarks and/or segmentation details may for example be marked, identified, or specified in the annotated preoperative image data. Synthetically simulated intra-operative training image data is then created automatically from the annotated preoperative image data of the patient to be examined. This may be done by a corresponding creation or simulation facility. The creation or simulation facility may be a conventional image processing or data processing facility or a further machine-learning facility trained accordingly. The second facility is then used for identifying the landmarks in the intra-operative image data of the patient to be examined and/or for its segmentation, wherein the facility is trained or retrained with the aid of the synthetically simulated intra-operative training image data.

The synthetically simulated intra-operative training image data is image data that in its properties or characteristics, at least essentially corresponds to conventional or typical intra-operative image data, for example, may include an image quality or the like typical of conventional intra-operative image data. For example, the synthetically simulated intra-operative training image data, as described for intra-operative image data, may include a lower or inferior image quality than the preoperative image data of the patient to be examined from which it has been created.

The second facility may be trained with the aid of the simulated intra-operative training image data from scratch, for example, from the ground up. However, a machine-learning facility that has been pre-trained with the aid of a plurality of intra-operative image data of other patients for identifying the landmarks and/or the segmentation is used as the starting point and is then retrained or adapted with the aid of the synthetically simulated intra-operative training image data of the specific patient to be examined. This provides the time needed, in the ultimate creation of the second facility during the application of the method, for example during the examination or treatment of the patient to be examined, to be kept particularly small or short.

To create the synthetically simulated intra-operative image data or training image data, automatically, starting from the annotated preoperative image data, different variations may be created, for example by random or statistical variation or changing of predetermined features or characteristics, by application of predetermined functions or functions or statistically varied actual values to the preoperative image data, by application of different effects or filters and/or more besides. The synthetically simulated intra-operative training image data may thus include a plurality of different variations that are created from the preoperative image data.

In this way a patient-specific fitting or overfitting of the second facility and at the same time a robust recognition of the landmarks and/or creation of the segmentation of the intra-operative image data of the patient to be examined may be obtained even if no or relatively little real, for example, non-synthetic training image data is available. The fact that the landmarks identified and/or the segmentation or segmentation details are already annotated or marked in the preoperative image data, that serves as starting point or starting basis for creation of the synthetically simulated intra-operative training image data, provides the synthetically simulated intra-operative training image data to be created automatically and to be used for training or for retraining the second facility. Even the synthetically simulated intra-operative training image data may thus be annotated. This provides this embodiment to be carried out effectively and with little effort and also during the examination or treatment of the patient to be examined in a gentle way for them, since it is done quickly.

In an embodiment, to create the synthetically simulated training image data, starting in each case from the annotated preoperative image data, a plurality of different deformations of imaged anatomical objects or features are simulated on the basis of at least one predetermined biomechanical model. If a specific organ, such as a liver, of the patient to be examined is imaged in the preoperative image data for example, then accordingly a biomechanical organ model, for example a biomechanical liver model, may be provided. Then for example, to create different synthetically simulated intra-operative training image data, parameters of the biomechanical model varied in a predetermined, random, or statistical way may be used for example. Then, with each different parameter value or each different set of parameter values, a deformation produced therewith may be simulated by the biomechanical model, for example, by running or executing the biomechanical model.

This simulation may then be applied to the preoperative image data in each case, whereby a variant of the synthetically simulated intra-operative training image data may then be produced in each case.

Likewise, a deformation simulated by the biomechanical model may be applied to the annotated preoperative image data. In this case for example image data contained in the annotated preoperative image data, for example segmented anatomical features of objects, for example organ boundaries or the like, may be deformed accordingly or fitted to the simulated deformation or fitted to the form simulated by the biomechanical model.

A number of different biomechanical models may be used. Thus, through the use of different biomechanical models, variations may likewise be created for the synthetically simulated intra-operative training image data. Likewise, different biomechanical models may be provided for different organs or anatomical features or regions. Then, if a number of organs or anatomical features or regions are imaged in the preoperative image data, the biomechanical model intended for this purpose may be used in each case for simulation of the respective deformation. This may improve a realism or realistic nature of the synthetically simulated intra-operative training image data.

The use of the at least one biomechanical model provides the synthetically simulated intra-operative training image data to be created realistically. Thus, the second facility may then be trained in a precise and robust manner, whereby ultimately a precise, reliable, and robust registration may be achieved. In this way, through the at least one biomechanical model, effects or situations may be taken into account for example that cannot readily be taken into account or simulated solely by random or statistical variation of image values or image elements, in for example a pneumoperitoneum, different stiffness in different tissues or tissue regions, anatomical boundary conditions, such as for example anatomically-related maximum displacements or deformations, different elasticities and/or more besides.

In an embodiment, to create the synthetically simulated intra-operative training image data, starting in each case from the annotated preoperative image data, image artifacts, for example a plurality of different types and/or arrangements and/or versions of image artifacts, and/or noise effects are simulated, that may occur during recording of intra-operative image data. This may be carried out for example, for example automatically, by or on the basis of corresponding predetermined functions, patterns, models, filters and/or more besides. The potential is provided of creating a large number of different variations of synthetically simulated intra-operative training image data and thereby of creating a broad training basis for the second facility. In this case no significant time outlay is needed and an extensive or at least essentially complete automation is possible.

In an embodiment, to create the synthetically simulated intra-operative training image data, starting in each case from the annotated preoperative image data, a weaker level of contrast and/or an incomplete filling of an imaged vascular tree with a contrast medium, for example in a plurality of different variations, is simulated. This may be done, for example automatically, as described for example by or on the basis of a corresponding predetermined function, a pattern, a model, and/or more besides. Different levels of contrast or contrast ratios may be simulated easily and quickly for example by a conventional imaging facility or by imaging software. Different fillings of the vascular tree may be simulated for example by a descriptive flow or propagation model. In this case for example an amount or concentration of the contrast medium, a flow speed, one or more vessel diameters, vessel constrictions or vessel narrowings and/or more besides may be simulated. This embodiment may lead or contribute to a more robust and more reliable adaptation of the second facility and thus ultimately to a more robust and more reliable registration.

In an embodiment, a deep neural net is used as at least one of the machine-learning facilities with an input layer, an output layer and at least one intermediate layer lying between them, also referred to as a hidden layer. Artificial neural networks may be effective and flexibly adaptable for carrying out the method described. For example, such neural networks, after their initial creation, only need little manual outlay, so that methods may be applied effectively and easily.

In an embodiment, at least one of the machine-learning facilities mentioned, that is different from the first facility, is pre-trained with the aid of image data of a plurality of different patients and is then retrained overfitted specifically to the patient to be examined and/or to their anatomical variant. An amount of time needed for the application of the method is reduced, since the overfitting or the retraining of the at least one facility is typically possible more quickly and with less effort than the creation of an equally trained facility from scratch or from the ground up, for example, for example starting from an initialization with random weights or parameter values. The robustness, for example in the recognition of the anatomical landmarks in the intra-operative image data of the patient to be examined and/or in their segmentation is improved by the overfitted retraining by comparison with conventional universal machine-learning facilities, for example, those trained where possible without patient-specific or variant-specific bias.

In an embodiment, a segmentation of at least one anatomical structure, an outline of an imaged organ and/or of at least one vessel, is carried out in the preoperative image data and/or in the intra-operative image data of the patient to be examined. The segmentation is done in such cases in addition to the recognition of landmarks and/or of the anatomical variant, that is carried out by at least one of the machine-learning facilities. The segmentation is then used in the method. Depending on the embodiment of the method, the segmentation may be used for example as an additional reference for the registration, in determining the anatomical variant and/or in evaluating the similarity, for example, during evaluation or as an additional part of the similarity criterion or the measure of similarity and/or more besides. This segmentation may be carried out or created in such cases with conventional methods and/or, as described, with at least one machine-learning facility. The additional taking into account or use of such a segmentation initially appears redundant, but in accordance with a finding may further improve the accuracy or robustness of the method.

Embodiments also provide a method, for example a computer-implemented method, for providing a set of machine-learning facilities, for example trained facilities, for a method for registration of preoperative image data of a patient to be examined with pre-operative image data of the patient to be examined. Annotated training image data provided, that includes pre-operative image data and less high-quality real or simulated intra-operative image data by comparison therewith, is received via a first interface and supplied in each case to at least one of the machine-learning facilities as input data. Output data created by processing of the input data by the respective facility is captured via a second interface. The facilities are trained in accordance with a predetermined training function on the basis of the input data and the output data. Training mechanisms known per se, for example backpropagation, may be applied. The set of correspondingly trained facilities is then provided via a third interface for use in the method for registration of image data. For better understanding this method is also referred to as the training method. The machine-learning facility may be trained by corresponding variants or embodiments of the training method, wherein the types of input data and output data described may be used in each case.

In the training image data provided for the training method, the predetermined anatomical landmarks or features in each case or an anatomical variant contained therein and/or a segmentation or segmentation details may be annotated or marked. By the training method the first machine-learning facility may be trained with the aid of pre-operative image data to detect the landmarks and/or the respective anatomical variant and/or to create or carry out a segmentation. The third machine-learning facility may likewise be trained accordingly by the training method. The second machine-learning facility may be trained by the training method, with the aid of intra-operative image data for the respective patient to be examined and/or for a specific anatomical variant of the patient to be examined, to identify the landmarks in the intra-operative image data and/or to create or carry out the segmentation of the intra-operative image data. The same applies to the is different variants or instances of the machine-learning facilities.

Embodiments also provide a computer program product, that includes commands or control instructions, that when executed by a computer, for example by an apparatus, cause the computer or the apparatus to carry out, for example automatically, at least one variant of the method. The computer program product may be a computer program or program code by which the method steps or sequences of the method are implemented, encoded, or represented. The computer program product may likewise be a computer-readable storage medium or a computer-readable data medium on which a corresponding computer program or corresponding program code is stored.

A further aspect is an apparatus that is configured to carry out, for example automatically, at least one embodiment of the method. The apparatus may accordingly thus be interpreted as a registration apparatus and/or as a training apparatus. The apparatus is configured for carrying out the method or methods. Accordingly, the apparatus may for example be the apparatus mentioned in conjunction with the method. The apparatus may thus be configured in the way described in conjunction with the method. For example, the apparatus may include a computer program product, in the form of a computer-readable data medium with a computer program stored thereon, that represents or encodes, for example, implements, the method steps of at least one of the methods.

The apparatus may include a processor or a processor facility, for example a microprocessor, microchip or controller, a hardware circuit, or an integrated circuit and/or more besides, for execution of the corresponding computer program or program code. The apparatus may include one or more data interfaces and/or user interfaces for receiving and/or outputting of data. The apparatus may be configured as a universal computer, that may execute a few or all steps or sequences of the respective method. The apparatus may include respective individual modules or facilities, that may each execute one or more of the sequences or method steps. For their part these modules or facilities may include their own computer-readable data medium and/or their own processor or their own processor facility in this case.

The apparatus may include a first training interface as a training apparatus for example, that is configured for receiving input training data, for example the training image data mentioned. The training apparatus may further include a second training interface, that is configured for receiving output training data, that is created depending on the input training data or correlated with the data or from the data. The training apparatus may further include an arithmetic unit or data processing facility, that is configured for training a function or a machine-learning facility based on the input training data and the output training data. The training apparatus may further include a third training interface, that is configured for outputting or providing the trained function or the trained machine-learning facility.

The characteristics and developments of the method specified previously and below, the apparatus and the computer program product as well as the corresponding advantages are able to be transferred in each case by analogy between the aspects of the embodiments.

BRIEF DESCRIPTION OF THE FIGURES

Further features, details, and advantages emerge from the description given below of embodiments as well as with the aid of the drawings. In the figures.

DETAILED DESCRIPTION

Figure 1:
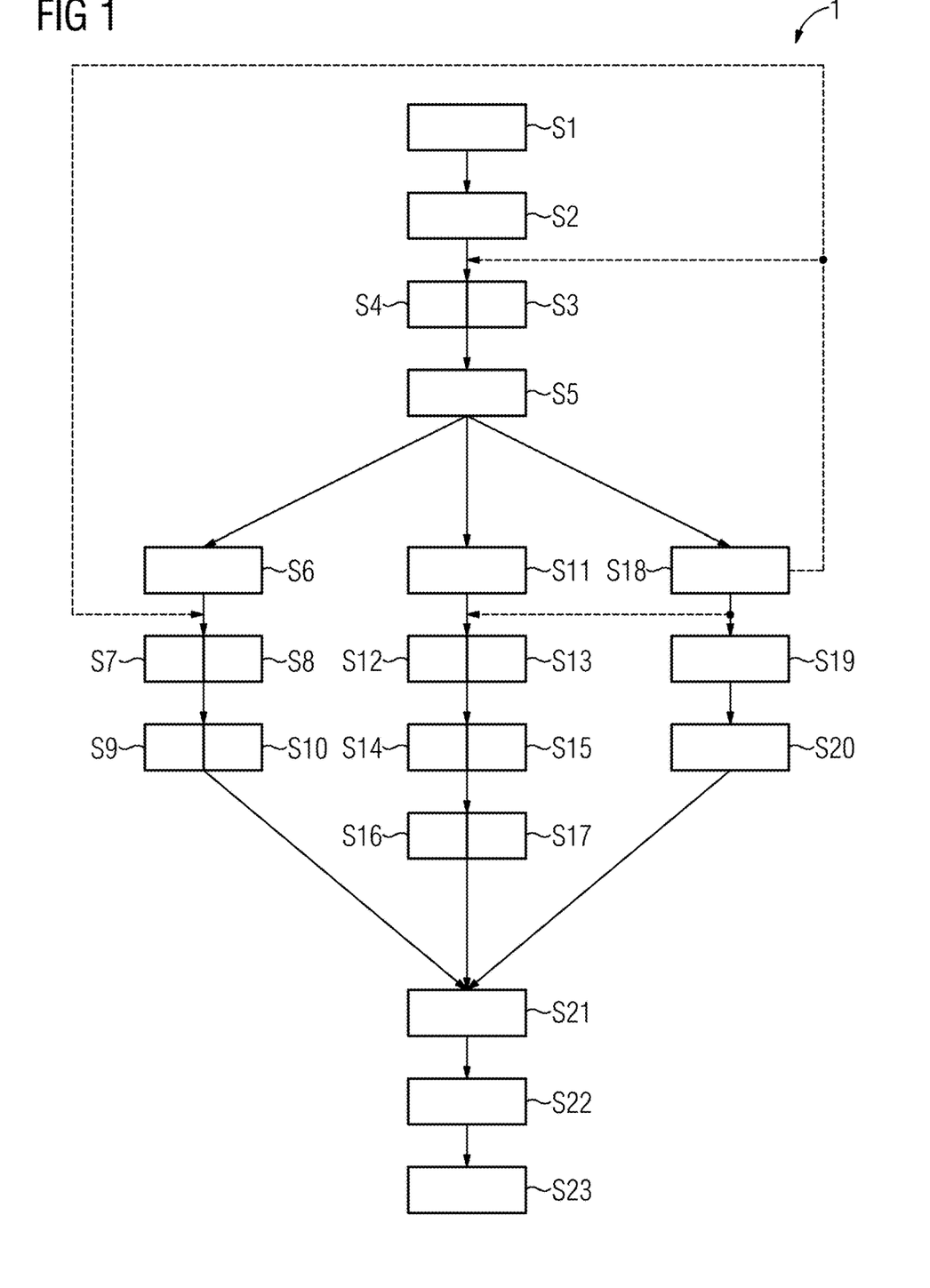
FIG. 1 depicts an example of a schematic flow diagram of a method for the registration of image data according to an embodiment.

FIG. 1 depicts an example of a schematic flow diagram 1 for a method for the registration of image data with one another, for example within the framework of medical imaging. During an examination, operation or intervention, an intra-operative CT, for example DynaCT or ultrasound imaging or the like, is to be registered to a preoperative dataset, for example a CT or MR dataset. The intra-operative imaging may include a lower or inferior image quality than the preoperative dataset.

A vascular tree of a liver may be imaged or will be imaged in each case for example. In such a case a geometrical location of anatomical structures may be important, for example to enable specific vessels to be reached precisely surgically or with an instrument, for example a needle or the like. The anatomical variability to be observed in practice may be problematic in such cases, for example of organs such as the liver. Anatomical structures or organs of different people that are nominally the same may be imaged differently or different people may include different anatomical structures within the same organ. In this sense there is thus not just the liver or one liver of which the images may always be registered reliably according to a predetermined scheme in the same way, but for example a plurality of different liver vascular trees, that may look entirely different from person to person.

Where a machine-learning facility is to be used it may moreover be problematic that typically only a relatively small amount of training data is available, that does not always make possible a sufficiently robust training for creating a universal machine-learning facility for registering the image data of additional anatomical variants. Thus, although an attempt may be made for example to train the machine-learning facility universally or generally for recognition of anatomical landmarks or features, this however often leads in practice to less robust registration results, since from person to person there may be different and/or differently arranged anatomical landmarks, of the vascular tree for example.

Figure 2:
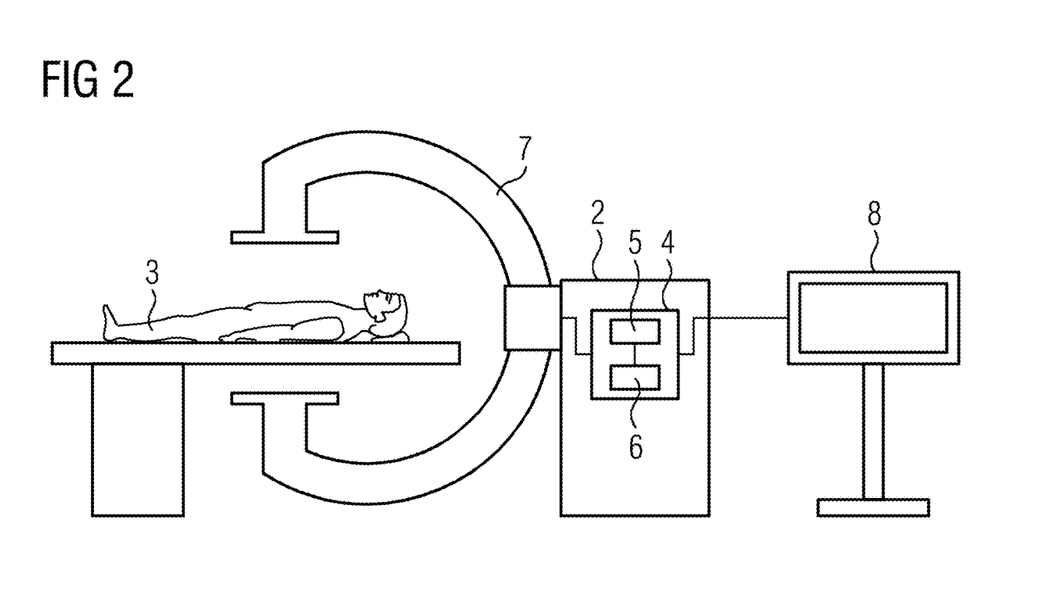
FIG. 2 depicts a schematic diagram of an apparatus for carrying out the method according to an embodiment.

The method will be explained below with the aid of the flow diagram 1 and its method steps S1 to S23 as well as with regard to FIG. 2 and FIG. 3. In this regard FIG. 2 depicts a schematic diagram of an apparatus 2 for carrying out the method. The apparatus 2 is also configured by way of example for recording of image data, in the present case of a specific patient to be examined 3. The apparatus 2 includes a data processing facility 4 with a processor 5 and a data memory 6 connected thereto. A program code or a computer program, that implements the method in accordance with the flow diagram 1 for example and is able to be executed by the processor 5, may be stored in the data memory 6 for example. The method steps shown in FIG. 1 may accordingly also represent program steps, program modules or functions of the corresponding computer program or program code.

The data processing facility 4 may carry out the method with the aid of image data of the patient 3, that is provided or retrieved for example via an interface, is provided in the data memory 6 and/or is recorded or created entirely or in part by an imaging device 7 shown schematically of the apparatus 2. Results or output data created by the data processing facility 4 may then for example likewise be stored in the data memory 6 and/or output via an interface, for example to a display facility 8 likewise indicated.

Figure 3:
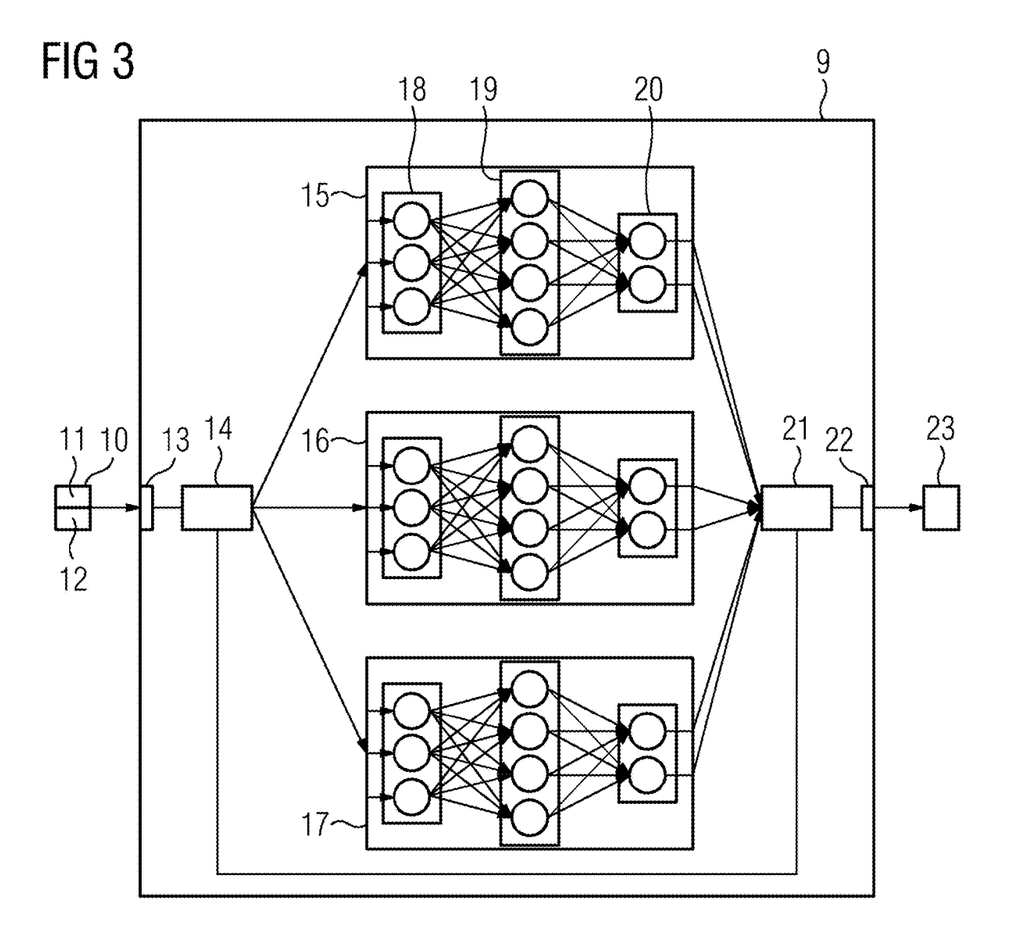
FIG. 3 depicts a schematic diagram of the method and the apparatus according to an embodiment.

FIG. 3 depicts a schematic diagram of a subsystem 9, of the data processing facility 4 for example. The subsystem 9 is configured to receive image data 10 as input data. In the present case this may be preoperative image data 11 and intra-operative image data 12 of the patient 3. This image data 10 is received, for example, captured, via an input interface of the subsystem 9. The received image data 10 may then be pre-processed for example by a pre-processing facility 14. for example, a kind or a type of the image data 10 is determined automatically and/or the image data 10 or specific parts of thereof may be forwarded, selectively for example. During a training phase an automatic or part automatic annotation of the received image data may likewise be carried out by the pre-processing facility 14 for example. The image data 10 may be forwarded, for example, provided, by the pre-processing facility 14 to a first neural network 15, a second neural network 16 and/or a third neural network 17. The neural networks 15, 16, 17 here are examples of purely schematic representations for machine-learning facilities. Artificial deep convolutional neural networks may be used.

In addition, or as an alternative one or more other machine-learning facilities might likewise be used.

The neural networks 15, 16, 17 each include a number of layers. For the sake of clarity only an input layer 18, a hidden intermediate layer 19 downstream thereof and an output layer 20 for the first neural network 15 are shown for the first neural network 15. Further layers and structures may likewise be provided and the neural networks 15, 16, 17 may likewise include different numbers of layers and/or different structures.

The layers 18, 19, 20 include a number of nodes, for example, artificial neurons, in each case. The nodes of at least adjacent of the layers 18, 19, 20 are linked to each other in such cases by edges, for example, directed connections. The numbers of the nodes and edges are likewise to be understood purely as schematic or by way of example, where the number of the nodes in the input layers 18 may correspond to the respective kind of input data provided to the respective neural network 15, 16, 17 and/or to features contained therein and a number of nodes in the output layers 20 may correspond to a type of output data to be provided or created by the respective neural network 15, 16, 17, to features contained therein, to a predetermined classification or class structure and/or more besides.

In a manner known per se, weights or weighting factors, filters, one or more activation functions, such as for example the Sigmoid function and/or one or more besides may be stored or encoded in the neural networks 15, 16, 17, whereby a behavior and a function of the respective neural network 15, 16, 17 will be defined or determined.

Output data provided or created by the neural networks 15, 16, 17 may be post-processed by a downstream post-processing facility 21 of the subsystem 9. This may for example include sorting, storage, combination and/or more besides of the respective output data. Correspondingly created result data 23 may be provided or output via an output interface 22 of the subsystem 9, for example to a data memory 6 or to the display facility 8 and/or to one or more further functions, systems, or subsystems.

The subsystem 9 may be executed in each case entirely or in part in hardware as part of the processor 5, and/or in software, for example stored in the data memory 6.

In method step S1 training data may be created or provided. The training image data may be medical image datasets of a plurality of different patients for example, that may be annotated—manually, automatically, or semi-automatically—in each case. The training image data may be collected together in a training database for example, that includes a plurality of datasets of individual patients. For each patient or for each dataset preoperative and also intra-operative scan or image data 10 of the respective patient may be present in the training database in this case. For example, the predetermined anatomical landmarks or a respective anatomical variant and/or a segmentation or segmentation details may be annotated therein. For example, a vascular tree may be shown in each case, wherein vessel branches—at least of larger vessels relative to a predetermined absolute or relative threshold value—a respective landmark or a marked course of the vessels may be a segmentation detail.

Where necessary, in method step S2, in addition or as an alternative, a segmentation of the training image data may be carried out, for example to identify or to define boundaries of organs or tissue regions.

In addition to this training image data based on real patients or on image data 10, synthetically created or simulated image data may be provided for an additional or supplementary training for example.

In method step S3 a first machine-learning facility, for example the first neural network 15, is trained with the aid of the training image data provided. The first neural network 15 may be trained for example automatically to assign to a patient dataset of image data 10 of a patient the anatomical variant occurring therein. Likewise, the first neural network 15 may be trained for example to carry out or to make possible an automatic detection or recognition of predetermined anatomical landmarks, for example, characteristic structures, such as for example specific vessels or vessel branches and/or a segmentation into preoperative image data.

In parallel thereto for example, in method step S4, a second machine-learning facility, for example the second neural network 16, and/or a third machine-learning facility, for example the third neural network 17, may be trained or pre-trained. This may be done in a similar way to the training of the neural network 15. For example, for training the first neural network 15 and for training the third neural network 17 the preoperative image data 11 and for training the second neural network 16 the intra-operative image data 12 may be used.

The training steps described above and below may be carried out by the data processing facility 4, for example by the subsystem 9. To this end the post-processing facility 21 includes a data connection to the pre-processing facility 14, via which output data of the neural networks 15, 16, 17 may be provided to the facility as input data, in order to make possible an iterative fitting, for example, an iterative training.

For the specific patient to be examined 3, their relatively high-quality preoperative image data 11 is then captured or loaded and in method step S5 is provided to the first neural network 15 and processed by the latter. Via this use of the first neural network 15, depending on its embodiment, the anatomical variant of the patient to be examined 3 may be determined and/or—where present—the predetermined anatomical landmarks of the patient to be examined 3 are detected or marked or annotated. Likewise, the preoperative image data 11 of the patient to be examined 3 may be segmented, for example, by the first neural network 15 or by a further facility, in order to detect or to determine a vascular tree or individual vessels, organ boundaries and/or more besides. For example, an outline of the liver may be detected and segmented, as a reference for later method steps for example and/or to determine the organ size and/or organ shape.

In an embodiment, in step S6, the datasets or patients that fulfill a predetermined similarity criterion or measure of similarity in relation to the specific patient to be examined 3, are thus sufficiently similar thereto, are determined from the training database. To determine such a measure of similarity for example an occurrence of specific landmarks and/or segmentation details in the respective dataset or spatial position relationships to one another may be evaluated. This may be carried out automatically for example by the data processing facility 4. The patients are looked for in the datasets, for example in the preoperative image data 11 of the training database, whose imaged anatomy is as good a match as possible to that of the specific patient to be examined 3. Whether the measure of similarity lies above a predetermined threshold value may be used for example as a selection and/or inclusion criterion for the datasets. Likewise, for example a predetermined number, depending on the size or scope of the training database, for example 100 or 1000, of the patients or the datasets with the highest measure of similarity of the highest degree of fulfillment of the similarity criterion may be selected.

For definition or determination of the anatomical variant and/or for determining or evaluating the measure of similarity or similarity criterion, as described, vessel branches may be included. Likewise, however, the size and/or shape of the respective organ considered, a texture of the tissue in the respective image dataset, a size of one or more vessels, an image quality of the respective image dataset, a recording device and/or recording protocol used for recording the respective image dataset, a presence and/or content of manual annotations and/or more besides may be used. Manual annotations may specify for example whether a previous operation, for example an embolization or the like has been carried out for the respective patient being imaged, whether chemotherapy has been undertaken or whether a cirrhosis of the liver, a fatty liver or the like is present, and so forth. The training image data may thus be determined that is similar to the patient to be examined 3 and includes characteristics or images features such as are to be expected for intra-operative image data 12 of the patient to be examined.

In addition to the similar datasets determined and selected, corresponding synthetic simulated image data, synthetic simulated intra-operative image data, may be provided. This may be created synthetically with corresponding characteristics or features and thus include a particularly great or adjustable similarity to the patient to be examined 3.

The similar datasets selected and also where necessary the synthetic simulated image data are then provided as training data. With the aid of this training data, in method step S7, the second neural network 16 and in method step S8 the third neural network 17 are trained or retrained. Because of the similarity of the training data used to the patient to be examined 3, an overfitting to the patient or to their anatomical variant or to their anatomical landmarks takes place. The second neural network 16 is trained for recognition of anatomical landmarks in intra-operative image data 12 or for their segmentation, for which for example the intra-operative image data 12 from the selected training image data may be used. The third neural network 17 is trained for identifying the same predetermined anatomical landmarks in the preoperative image data 11 and/or for carrying out or creating their segmentation, for which for example the preoperative image data 11 from the selected datasets of the training image data may be used.

The intra-operative image data 12 of the specific patient to be examined 3 is recorded or captured or loaded, for example by the imaging device 7 or from the data memory 6.

In method step S9 the trained or retrained second neural network 16 is applied to the intra-operative image data 12 of the patient to be examined 3. Through this application of the second neural network 16 the anatomy-specific landmarks of the patient to be examined 3 are identified and/or the landmarks are segmented. As also in the other applications for example, there may be a marking, segmentation and/or a determination of position or coordinates of the landmarks and/or of segmentation details. Where necessary the intra-operative image data 12 of the patient to be examined 3 may be segmented manually or automatically in addition to the recognition of the anatomical landmarks, for example by the data processing facility 4.

In method step S10 the trained or retrained third neural network 17 is applied for recognition of the same anatomical landmarks and/or for segmentation to the pre-operative image data 11 of the patient to be examined 3. Through this the same anatomy-specific or patient-specific anatomical landmarks and/or the same anatomical features or segmentation details are identified in the pre-operative image data 11 of the patient to be examined 3 as were identified in method step S9 in the intra-operative image data 12.

The second neural network 16 and the third neural network 17 may be pre-trained for example on the basis of all patients or all available training image data, then fitted or adapted however by a retraining to the selected datasets of the specific anatomical variants or the patients determined as being similar, whereby an overfitting is performed on the corresponding anatomical version. This provides the anatomical landmarks to be identified robustly and reliably for the specific patient to be examined 3 by the retrained neural networks 16, 17, for example by comparison with conventional universal neural networks.

In an embodiment, in method step S11 those anatomical variants are determined or established in the training image data, that at least occur with a predetermined frequency, for example, that fulfill a relative or absolute predetermined frequency criterion for example. For each of these anatomical variants determined the associated datasets are then provided separately or are provided or used as separate bundles on variant-specific training image data. In addition, synthetic simulated image data may be created and likewise provided or used as part of the respective variant-specific training image data.

In method step S12, for a number of or for all of the variants determined, a respective instance of the second neural network 16 may be trained or retrained, for example, for example fitted or adapted. In this case the variant-specific training image data, for example its intra-operative image data 12, is used. The different instances of the second neural network 16 are thus trained to identify the predetermined anatomical landmarks in intra-operative image data 12 of the respective segmentation and/or to create a segmentation of such intra-operative image data 12. The respective instances of the second neural network 16 may thus identify the predetermined anatomical landmarks and/or create the segmentation robustly and reliably in intra-operative image data 12 for the respective anatomical variant.

In a similar way, in method step S13, a respective instance of the third neural network 17 is trained or retrained for each of the determined anatomical variants. The preoperative image data 11 of the respective sets or bundles of training image data of the respective variant is used as training data. The different instances of the third neural network 17 are thus trained variant-specifically to identify the same predetermined anatomical features in preoperative image data 11 of the respective anatomical variant as are identified or may be identified by the instances of the second neural network 16 in intra-operative image data 12.

In a method step S14 the instance of the second neural network 16 is determined and selected that has been trained for that anatomical variant that was determined in method step S5 for the specific patient to be examined 3. In a similar way, in a method step S15, that instance of the third neural network 17 is determined and selected that has likewise been trained for this anatomical variant.

In a method step S16 the selected instance of the second neural network 16 is applied to the intra-operative image data 12 of the patient to be examined 3 and thereby where necessary the anatomical landmarks contained or imaged therein are identified. In addition, or as an alternative, the segmentation of the intra-operative image data 12 of the patient to be examined 3 may likewise be carried out. In a similar way, in method step S17, by the selected instance of the third neural network 17, the anatomical landmarks in the preoperative image data 11 of the patient to be examined are identified and/or their segmentation is created.

The instances of the neural networks 16, 17 selected may likewise be used as pre-trained starting points for respective retraining of the neural networks 16, 17 in the method steps S7 or S8. Where necessary this may further improve the fitting and thereby the patient or variant-specific robustness of the landmark recognition and/or segmentation or segmentation creation.

In a few application cases or situations for example the anatomical variance occurring in practice, for example, diversity of variants, may be so great and/or the available amount of training image data so small that the variant-specific training or retraining of the individual instances may be difficult. In such a case the previously described similarity-based first embodiment of the method and/or a third embodiment of the method described below may be applied to good effect.

In the alternative or combinable third embodiment of the method, in a method step S18, on the basis of the preoperative image data 11 of the patient to be examined 3, for example, starting from the preoperative image data 11, synthetic simulated intra-operative image data 11 is created. For example, this may be created as annotated synthetic intra-operative training image data. The annotation in this case may be based on or given by or as the annotation or marking created of the preoperative image data 11 of the patient to be examined 3 created by the first neural network 15. For example, synthetic annotated DynaCT training data, for example, simulated, or virtual DynaCTs, may be created on the basis of the complete or relatively higher-quality preoperative CT dataset of the patient to be examined 3. Likewise, virtual intra-operative MR images may be created for example from a preoperative MR dataset.

A plurality of possible deformations, for example based on at least one biometric model, may be simulated, preferably taking into consideration the pneuomoperitoneum, in order to create different variations, for example, different synthetic simulated intra-operative image data. In such cases corresponding landmarks and/or segmentation details or their annotations may be moved as well according to the simulated deformation. This provides the relative accuracy of the identification or annotation as well as the presence of the landmarks and/or segmentation details to be maintained. Likewise, for example image artifacts, a reduced image quality and/or noise, as are typically experienced in intra-operative image recordings or image data, may be simulated in this step. Further for example a lower level of contrast compared to the preoperative image data 11 and/or an incomplete filling of vessels with contrast medium may be simulated. These and/or further aspects may be statistically varied in this case, for example by the data processing facility 4 in accordance with a predetermined function or a predetermined pattern, in order to create a plurality of varied, for example, different synthetic simulated intra-operative image data.

Since the synthetic simulated intra-operative image data is created using the preoperative image data 11 of the patient to be examined 3 as its starting point, the synthetic simulated intra-operative image data is in this sense likewise accordingly patient or variant-specific.

In method step S19 the second neural network 16 is trained or retrained with the aid of the synthetic simulated intra-operative image data, in order to identify in intra-operative image data 12 of the patient to be examined 3 or the intra-operative image data 12, that images the anatomical variants of the patient to be examined 3, the predetermined landmarks, for example the specific anatomical landmarks present in the patient to be examined 3 and/or to create the corresponding segmentation or to identify the segmentation details present. An overfitting of the second neural network 16 to the specific patient to be examined 3 of to their anatomical variant is undertaken. Thus, despite a relatively small number or amount of real, for example, non-synthetic or non-simulated training image data, a robust and reliable recognition of these landmarks, features or segmentation details or a robust and reliable creation or carrying out of the segmentation at least for the respective specific anatomy may be achieved. The second neural network 16 may also be referred to as a template DNN (Deep Neural Network).

After recording of the intra-operative image data 12, for example of an intra-operative DynaCT with systemic contrast, of the patient to be examined 3, in a method step S20, the second neural network 16 trained or retrained in this way is applied to the data. Through this the corresponding anatomical landmarks and/or segmentation details are identified or detected in the intra-operative image data 12 of the patient to be examined. In addition, or as an alternative a segmentation of the intra-operative image data 12 of the patient to be examined 3 may also be carried out, to determine organ boundaries and/or further anatomical features or details, for example. For example, where the landmarks are identified by the second neural network 16, segmentation methods known per se may likewise be applied for the segmentation. For example, a manual or semi-automatic segmentation may be carried out or a further neural network or the like trained for the segmentation of image data may be used.

Regardless of the embodiment of the method selected, for example, used up to this point, in a method step S21, a for example elastic registration of the intra-operative image data of the patient to be examined 3 with the preoperative image data of the patient to be examined 3 may be carried out automatically on the basis of the anatomical landmarks identified in each case. This may be performed by the data processing facility 4. Where present, it may be that at least one of the described additional segmentations or data or information obtained therewith, for example the organ or tissue boundaries, may be taken into consideration, for example, used. The latter may make possible a further improved accuracy and reliability of the registration. For example, the registration may be carried out for example by the post-processing facility 21, so that the result data 23 may be created as the result of the registration for example. The result data 23 may for example be or include the registered combination or overlaying or the intra-operative image data 12 and the preoperative image data 11 of the patient to be examined 3.

In a method step S22 the result data 23 of the registration may be output via the display facility 8 for example and/or stored in the data memory 6 for example.

Depending on the situation or application case, in a method step S23, the result data 23 may be further processed or used. For example, based thereon, needle path planning, embolization guidance or the conducting of another therapy may be carried out or supported.

Unlike the examples shown and described, one or more sequences of the method steps described as well as a further combination of one or more method steps of the different embodiments of the method described may likewise be possible.

If for example a number of method steps or embodiments are combined with one another, the designations of the neural networks 15, 16, 17 described in connection with them may relate to the same neural network 15, 16, 17 in each case or additional neural networks may accordingly be meant and accordingly be used. For example, the first neural network 15 as such may be trained for the recognition of landmarks. If moreover a further neural network, that is derived from the first neural network 15 for example or may include a common preliminary stage with the network, is trained and used for recognition of the anatomical variants, then this further neural network may be referred to for example as a fourth neural network. If for example the second neural network 16 described in method step S7 and the third neural network 17 described in method step S8 are used, then for their additional use, the neural network selected in method step S14 may be referred to as the fifth neural network and the neural network selected in method step S15 may be referred to as the sixth neural network. In a corresponding way the neural network trained in method step S19 may be referred to for example as the seventh neural network for its additional use or application in one of the other embodiments of the method.

Overall, the examples described show how a robust registration of image data is possible despite anatomical variations and how in such cases synthetic patient or variant-specific training data may be created and used where necessary. In this case the extraction of features from the preoperative image data 11 of the specific patient 3 and the automatic obtaining of a registration algorithm suitable for the anatomy of the patient to be examined 3 based thereon for the intra-operative image data 12 or the training of a patient or variant-specific machine-learning facility on the basis of the preoperative image data 11 of the specific patient to be examined 3 may be understood as fundamental approaches.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for registration of a patient's preoperative image data with the patient's intra-operative image data, the method comprising:
    training a first machine-learning facility to identify predetermined anatomical landmarks present in preoperative image data;
    training a second machine-learning facility to identify in intra-operative image data the predetermined anatomical landmarks identified by the first machine learning facility, whereby an overfitting of the second machine-learning facility is performed on the predetermined anatomical landmarks, wherein the intra-operative image data is of a lower resolution or includes an inferior contrast ratio than the preoperative image data;
    identifying one or more predetermined anatomical landmarks in the patient's preoperative image data by the first machine-learning facility;
    identifying the one or more predetermined anatomical landmarks in the patient's intra-operative image data by the second machine-learning facility; and
    registering the patient's preoperative image data with the patient's intra-operative image data with an aid of the identified one or more predetermined anatomical landmarks by the first machine-learning facility and the second machine-learning facility, wherein the patient's intra-operative image data is of a lower resolution or includes an inferior contrast ratio than the patient's preoperative image data.

2. The method of claim 1, wherein the first machine-learning facility and the second machine-learning facility are trained to generate segmentations that are used when registering the patient's preoperative image data provided with the patient's intra-operative image data.

3. The method of claim 1, wherein a plurality of datasets of a plurality of patients is provided, wherein each of the plurality of datasets contains preoperative image data in each case, that are at least annotated with the respective anatomical variants present therein, and intra-operative image data assigned to these, in which at least the predetermined landmarks are specified as annotation, of precisely one of the plurality of patients;

wherein on a basis thereof anatomical variants are determined, that occur in datasets with at least a predetermined frequency in each case, wherein for each of the anatomical variants determined a respective variant-specific instance of the second machine-learning facility is provided that is trained or retrained in each case only with an aid of the intra-operative image data of the corresponding datasets in which the respective anatomical variant occurs;

wherein for each of the anatomical variants determined a respective instance of the first machine-learning facility is provided that is trained or retrained in each case only with an aid of the preoperative image data of the corresponding datasets in which the respective anatomical variant occurs;

wherein the anatomical variant of the patient to be examined is determined with an aid of the preoperative image data; and wherein for the recognition of the landmarks in the image data provided for the registration, trained instances of the first machine learning facility and second machine learning facility are selected and used for the anatomical variant determined of the patient to be examined.

4. The method of claim 1, wherein a plurality of datasets of a plurality of patients is provided, wherein each of the plurality of datasets contains preoperative image data and intra-operative image data assigned in which at least the predetermined landmarks are specified as annotations of at least one of precisely one of the plurality of patients;

wherein the predetermined landmarks are identified by the correspondingly trained first facility in the patient's preoperative image data;

wherein correspondingly similar datasets are determined and selected automatically from the plurality of datasets, that in accordance with a predetermined similarity criterion based on the identified landmarks, describe an anatomy similar to the patient to be examined;

wherein the second machine-learning facility is used for identifying the landmarks in the intra-operative image data of the patient to be examined, wherein the second machine-learning facility is only trained or retrained with an aid of the intra-operative image data from the selected similar datasets.

5. The method of claim 4, wherein whether in the datasets the landmarks identified in the preoperative image data of the patient to be examined or at least of a predetermined portion thereof determined in the preoperative image data of the patient to be examined is contained in the respective dataset is used as the similarity criterion.

6. The method of claim 4, wherein the similarity criterion used is a geometrical position relationship of a number of landmarks in relation to one another and/or to at least one predetermined anatomy feature or reference point.

7. The method of claim 1, wherein the one or more predetermined landmarks that are present in the patient's preoperative image data are identified by the first machine-learning facility, wherein on the basis thereof preoperative image data is annotated with the identified predetermined landmarks, wherein synthetic simulated intra-operative training image data is created automatically from the annotated preoperative image data, and wherein the second machine-learning facility is used to identify the one or more predetermined landmarks in the patient's intra-operative image data, wherein the second machine-learning facility is trained or retrained with an aid of the synthetic simulated intra-operative training image data.

8. The method of claim 7, wherein to create the synthetic simulated intra-operative training image data, starting from the annotated preoperative image data, a plurality of different deformations of anatomical objects or features imaged is simulated on the basis of at least one predetermined biomechanical model.

9. The method of claim 7, wherein to create the synthetic simulated intra-operative training image data, starting from the annotated preoperative image data, a plurality of different kinds, arrangements, or versions of image artifacts or noise effects are simulated, which may occur during the recording of intra-operative image data.

10. The method of claim 7, wherein to create the synthetic simulated intra-operative training image data, starting from the annotated preoperative image data, a weaker level of contrast or an incomplete filling of a vascular tree imaged with a contrast medium in a plurality of different variants, is simulated.

11. The method of claim 1, wherein a deep neural network with an input layer, an output layer, and at least one intermediate layer lying between the input layer and output layer is used as at least one of the machine-learning facilities.

12. The method of claim 1, wherein the second machine-learning facility is pre-trained with an aid of image data of a plurality of different patients and is then retrained overfitted specifically to the patient to be examined.

13. The method of claim 1, wherein a segmentation of at least one anatomical structure in the preoperative image data or in the patient's intra-operative image data, is generated by at least one of the machine-learning facilities.

14. The method of claim 1, further comprising:
providing annotated training image data that comprises preoperative image data and intra-operative image data; and
inputting the annotated training image data into each of machine-learning facilities as input data;
capturing output data created by processing of the input data by the respective machine-learning facilities;
training the machine-learning facilities with a predetermined training function on the basis of the input data and the output data, and
providing the machine-learning facilities.

15. A method for registration of a patient's preoperative image data with less the patient's intra-operative image data, the method comprising:
training a first machine-learning facility to generate a segmented image of predetermined anatomical landmarks in preoperative image data;
training a second machine-learning facility to generate a segmented image of the predetermined anatomical landmarks in intra-operative image data, whereby an overfitting of the second machine-learning facility is performed on the predetermined anatomical landmarks, wherein the intra-operative image data is of a lower resolution or includes an inferior contrast ratio than the preoperative image data;
segmenting one or more predetermined anatomical landmarks in the patient's pre-operative image data by the first machine-learning facility;
segmenting the one or more predetermined anatomical landmarks in the patient's intra-operative image data of the patient by the second facility, wherein the patient's intra-operative image data is of a lower resolution or includes an inferior contrast ratio than the patient's preoperative image data; and registering the patient's preoperative image data with the patient's intra-operative image data with an aid of the segmentations by the first machine-learning facility and the second machine-learning facility.

16. The method of claim 15, wherein a deep neural network with an input layer, an output layer, and at least one intermediate layer lying between the input layer and output layer is used as at least one of the machine-learning facilities.

17. The method of claim 15, further comprising:
providing annotated training image data that comprises preoperative image data and less high-quality intra-operative image data; and
inputting the annotated training image data into each of machine-learning facilities as input data;
capturing output data created by processing of the input data by the respective machine-learning facilities;
training the machine-learning facilities with a predetermined training function on the basis of the input data and the output data, and
providing the machine-learning facilities.

18. A method for registration of a patient's preoperative image data with the patient's intra-operative image data, the method comprising:
training a first machine-learning facility to identify an anatomical variant present in preoperative image data;
training patient-specifically for anatomical variants, a second machine-learning facility to identify predetermined anatomical landmarks in intra-operative image data, whereby an overfitting of the second machine-learning facility is performed on the predetermined anatomical landmarks, wherein the intra-operative image data is of a lower resolution or includes an inferior contrast ratio than the preoperative image data;
training a third machine-learning facility to identify in pre-operative image data the predetermined landmarks of a specific anatomical variant identified by the second machine-learning facility;
identifying the patient's anatomical variant in the patient's preoperative image data by the first machine-learning facility;
identifying one or more predetermined anatomical landmarks that are present in the patient's preoperative image data by a respective instance of the third machine-learning facility trained for the specific anatomical variant of the patient;
identifying the one or more predetermined anatomical landmarks in the intra-operative image data of the patient by the second machine-learning facility; and
registering the patient's preoperative image data with the patient's intra-operative image data with an aid of the identified one or more predetermined anatomical landmarks, wherein the patient's intra-operative image data is of a lower resolution or includes an inferior contrast ratio than the patient's preoperative image data.

19. The method of claim 18, wherein a plurality of datasets of a plurality of patients is provided, wherein each of the plurality of datasets contains preoperative image data in each case, that are at least annotated with the respective anatomical variants present therein, and intra-operative image data assigned to these, in which at least the predetermined landmarks are specified as annotation, of precisely one of the plurality of patients;

wherein on the basis thereof anatomical variants are determined, that occur in the plurality of datasets with at least a predetermined frequency in each case,
wherein for each of the anatomical variants determined a respective variant-specific instance of the second machine-learning facility is provided that is trained or retrained in each case only with an aid of the intra-operative image data of corresponding datasets in which the respective anatomical variant occurs;
wherein for each of the anatomical variants determined a respective instance of the third facility is provided that is trained or retrained in each case only with an aid of the preoperative image data of the corresponding datasets in which the respective anatomical variant occurs;
wherein the anatomical variant of the patient to be examined is determined with an aid of the preoperative image data provided of the patient to be examined by the first machine-learning facility; and
wherein for the recognition of the landmarks in the image data provided for the registration, trained instances of the second machine-learning facility and of the third facility are selected and used for the anatomical variant determined of the patient to be examined.

20. The method of claim 18 wherein a plurality of datasets of a plurality of patients is provided, wherein each of the plurality of datasets contains preoperative image data and intra-operative image data assigned in which at least the predetermined landmarks are specified as annotations of at least one of precisely one of the plurality of patients;
wherein the predetermined landmarks are identified by the correspondingly trained first machine-learning facility in the preoperative image data of the patient to be examined;
wherein correspondingly similar datasets are determined and selected automatically from the plurality of datasets, that in accordance with a predetermined similarity criterion based on the identified landmarks, describe an anatomy similar to the patient to be examined;
wherein the third machine-learning facility trained specifically for pre-operative image data of the anatomical variant to identify the predetermined anatomical landmarks is used for identifying the landmarks in the preoperative image data of the patient to be examined, wherein the third machine-learning facility is only trained or retrained with an aid of the preoperative image data from the selected similar datasets,
wherein the second machine-learning facility is used for identifying the landmarks in the intra-operative image data of the patient to be examined, wherein the second machine-learning facility is only trained or retrained with an aid of the intra-operative image data from the selected similar datasets.

21. The method of claim 20, wherein whether in the plurality of datasets the landmarks identified in the preoperative image data of the patient to be examined or at least of a predetermined portion thereof determined in the pre-operative image data of the patient to be examined is contained in the respective dataset is used as the similarity criterion.

22. The method of claim 20, wherein the similarity criterion used is a geometrical position relationship of a number of landmarks in relation to one another and/or to at least one predetermined anatomy feature or reference point.

* * * * *